United States Patent [19]

Balzano

[11] Patent Number: 4,948,951
[45] Date of Patent: Aug. 14, 1990

[54] HEATER EMPLOYING FLEXIBLE CIRCUITRY

[76] Inventor: Alfiero Balzano, 11762 Western Ave., Unit O, Stanton, Calif. 90680

[21] Appl. No.: 292,833

[22] Filed: Jan. 3, 1989

[51] Int. Cl.⁵ .............................................. H05B 3/34
[52] U.S. Cl. .................................... 219/528; 219/211; 219/544; 219/549
[58] Field of Search ............... 219/211, 527, 528, 529, 219/548, 200, 201, 544, 549

[56] References Cited

U.S. PATENT DOCUMENTS

| | | | |
|---|---|---|---|
| 1,275,451 | 8/1918 | Lillard | 219/211 |
| 3,569,666 | 3/1971 | Murphy | 219/211 |
| 3,906,185 | 9/1975 | Gross | 219/211 |
| 3,946,193 | 3/1976 | Giese | 219/211 |
| 3,977,093 | 8/1976 | Santroch | 219/211 |
| 4,204,110 | 5/1980 | Smit | 219/313 |
| 4,665,301 | 5/1987 | Bondy | 219/527 |
| 4,665,308 | 5/1987 | Courvoisier | 219/528 |

Primary Examiner—Bruce A. Reynolds
Assistant Examiner—Leon K. Fuller
Attorney, Agent, or Firm—Roger A. Marrs

[57] ABSTRACT

A heater is disclosed herein taking the form of an elongated length of flexible cable having an insulative base carrying a plurality of spaced-apart conductive strips as a unitary construction. The heater is used as an insert received into an article of clothing, such as a boot, shoe or glove, and includes a power source, control switch and stress relief strip configurations to protect the heater structure during flexure of the circuitry.

15 Claims, 2 Drawing Sheets

FIG. 4a.
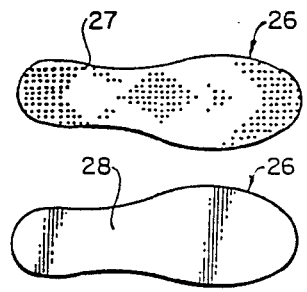
FIG. 4b.
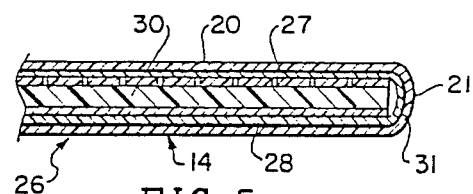
FIG. 5.
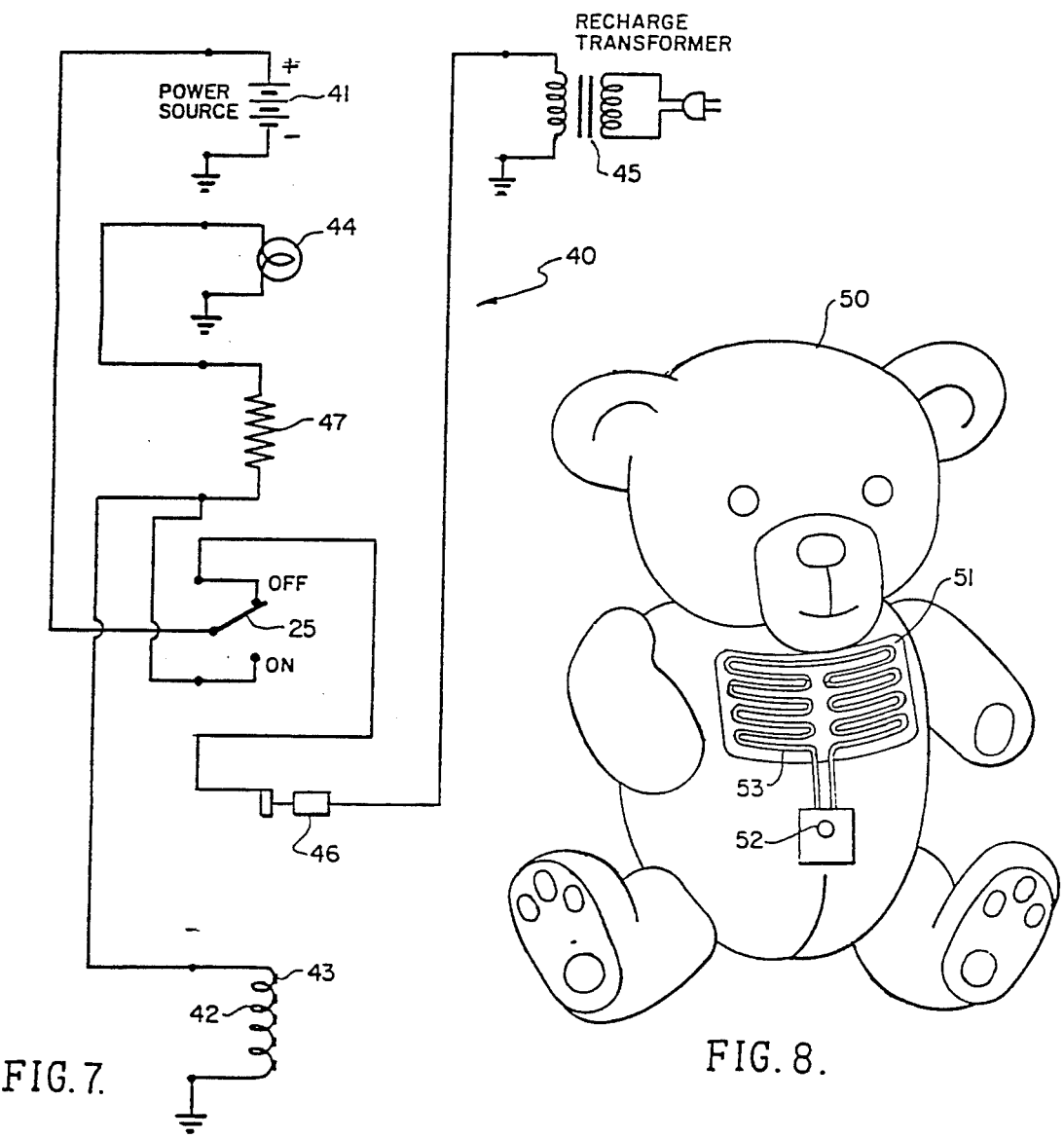
FIG. 7.
FIG. 8.

HEATER EMPLOYING FLEXIBLE CIRCUITRY

BACKGROUND OF THE INVENTION

1. Field of the Invention

The present invention relates to flexible heaters, and more particularly to a novel flexible heater adapted to be insertably received in gloves and boots or other wearing apparel for the purpose of heating a specified area and which will readily flex during movement of the person wearing the heater so that conductive circuits will not be broken or disrupted.

2. Brief Description of the Prior Art

In the past, it has been the conventional practice to provide a variety of heaters which employ wires that are directly embedded in various portions of clothing so that the wearer of the clothing will receive the benefit of heat. This has been particularly useful in the aviation industry where wires have been run through flying clothing as well as flying boots wherein the principles of electrical resistive heating are used. However, problems and difficulties have been encountered when employing such clothing with wire conductive paths that stem largely from the fact that wires readily break when flexed so that body movements of the wearer tend to sever electrical conductive paths disrupting the circuits. In such instances, the use of the device as a heater is completely eliminated and rendered useless for its intended purpose.

Other problems and difficulties have been encountered when dealing with wires that stem largely from the fact that wires as a conductive path for electricity are generally thick since each individual wire is of circular cross-section having a definite diameter. Also, because of the propensity of wire to break when bent during body movements of the wearer, the wires cannot be placed close together since short-circuiting may occur at any time. Even when heavy insulative material is placed between the wire conductors, severing of the conductor will oftentimes cause the wire to engage with adjacent wires to cause the short circuit. It is relatively easy for a severed wire conductor to protrude through adjacent insulative material since the breakage of a wire leaves sharp edges that may cut or sever the insulation.

Furthermore, historically, wire conductors do not provide suitable strain relief during pulling or flexing body movements of the wearer so that the wires may readily be flexed to the point of breakage or, literally, the wire conductors are pulled from sockets, power source, switch connections or the like.

Therefore, a long standing need has existed to provide a novel heater that is composed of a unitary insulative and strip-conductive paths which are of unitary construction so that the heater may be readily slipped or introduced into wearing apparel such as boots or gloves. The flexible conductive circuits should be provided with a strain relief means so that normal body movements of the wearer will not fatigue the conductors nor cause inadvertent breakage thereof.

SUMMARY OF THE INVENTION

Accordingly, the difficulties and problems described above are obviated by the present invention which provides a novel heater constructed from a unitary structure of insulative material and conductive strips arranged in spaced-apart relationship wherein the conductors are elongated strips of conductive material having portions folded over upon themselves at respective joint locations so as to accommodate body movement without undue stress. The conductive strips are arranged in a pattern substantially covering or outlining the body portion intended to be heated and substantially following the contour of the wearing apparel into which the heater is inserted. Suitable power source means is operatively coupled to the conductive circuits for providing electrical resistance heating and the power source may be selected from a variety of energy sources such as rechargeable batteries, storage cells, piezoelectric crystals or the like.

Additionally, an innersole may be incorporated with the heater so that moisture control and a cushioning effect are produced, as well as heating, so that total environmental control is achieved. Preferably, the innersole is perforated on its top side and employs a solid surface on its opposite side with the flexible conductive heater circuitry adapted to be folded about the innersole so as to be carried therewith for insertion purposes into wearing apparel of the user.

Therefore, it is among the primary objects of the present invention to provide a novel heater construction incorporating flexible circuit having a base of insulative material preformed with a plurality of electrically conductive strips embedded therein so that the heater is flexible in its operative electrical conducting condition without being subjected to breakage and disruption of the electrical circuit.

Another object of the present invention is to provide a novel heater construction incorporating flexible cable which integrally incorporates stress relief means so that the heater may be flexed to accommodate normal body movements without rupture or disconnection of the electrical circuit.

Yet another object of the present invention is to provide a relatively inexpensive and easy to use heater composed of a unitary construction of flexible material and conductive strips in the form of a flexible circuit that is flat and which incorporates strain relief means to prevent disruption of the electrical circuit.

Yet another object of the present invention is to provide a novel innersole for carrying a heater composed of flexible circuit as a unitary construction that may be readily inserted into wearing apparel of a user so that total environmental control is gained over temperature and moisture conditions within the article of wearing apparel.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 4 illustrates an innersole usable with the flex circuit heater of the present invention;

FIG. 5 is an enlarged fragmentary cross-sectional view of the innersole shown in FIG. 4 incorporating the novel flex circuit heater of the present invention;

FIG. 7 is a circuit diagram illustrating an operable electrical circuit for supplying power to the heater of the present invention; and FIG. 8 is still another version of the present invention wherein the flex circuit heater is employed in connection with a toy or novelty item.

DESCRIPTION OF THE PREFERRED EMBODIMENT

Figure 1:
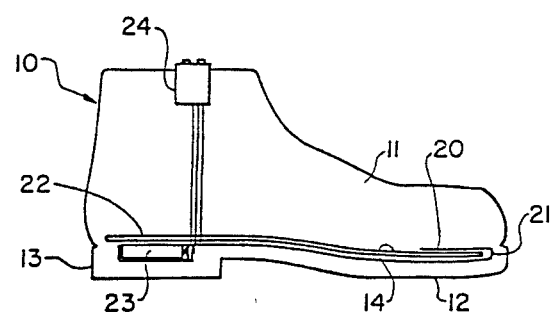
FIG. 1 is a diagrammatic view showing a boot having the novel flex circuit heater of the present invention inserted therein.

Referring to FIG. 1, a boot is indicated by numeral 10 which includes a boot top 11 and a sole 12 which terminates in one end at a toe and at its opposite end with a heel 13. The flexible circuit heater of the present invention is indicated in general by numeral 14 and includes a length of insulative material embedding a plurality of spaced-apart electrical connective strips so that a thin film or layer of plastic material embeds the conductive strips whereby the flex or flexible circuit is unitary in construction and may be readily folded over upon itself without breaking or severing the electrical conductors. The flexible or flex circuit or cable comprises a plurality of parallel and spaced-apart electrical conductors, such as indicated by numerals 15 and 16 in FIG. 2 which are carried between sheets of plastic constituting insulation so that the insulation separates adjacent conductors and holds the respective conductors in position with respect to one another as a unitized element or article.

Figure 2:
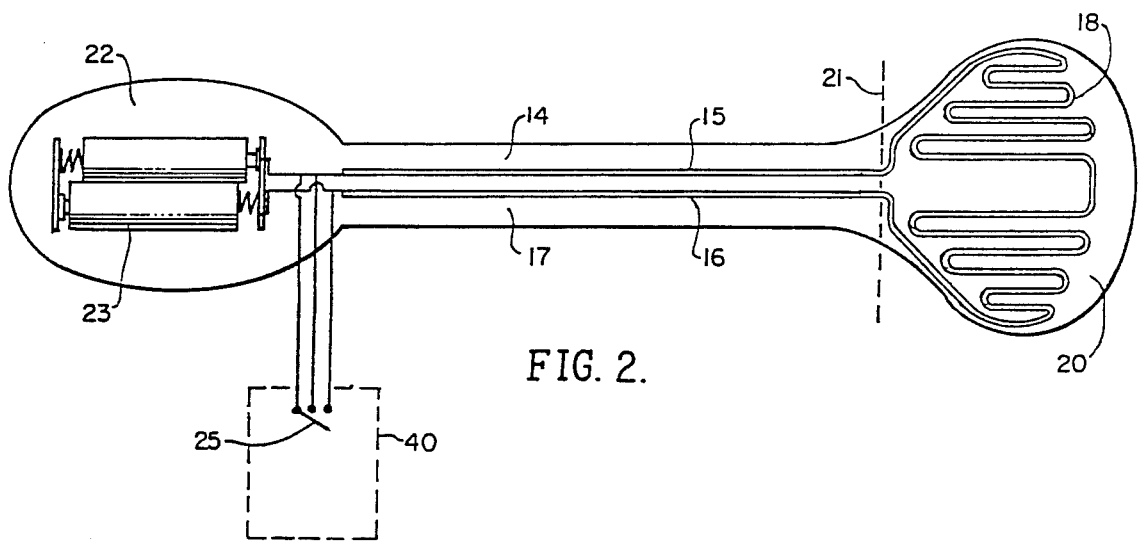
FIG. 2 is an enlarged plan view of the novel flex circuit heater shown in connection with the boot of FIG. 1.

Referring specifically to FIG. 2, the electrical conductors of the flex circuit 14 constitute bus lines along the midsection or central part of the circuit, as indicated broadly by numeral 17, and terminates at one end constituting a toe area in a tortuous or folded over path of electrical conductors forming a parallel pattern of loops, as broadly indicated by numeral 18. The toe area or portion is indicated by numeral 20 and a fold line is indicated by numeral 21 whereby the heater may be folded over upon itself so that the toe area 20 rests on top of a portion of the midsection 17. The foldover is more clearly shown in FIG. 1 wherein the toe portion 20 will underlie the toes and perhaps the ball of the foot of the user when the boot 10 is being worn. It is to be borne in mind that the heater 14 is substantially flat and is of thin or narrow thickness and that each of the conductor strips is flat and is of substantial reduced thickness as compared to the diameter of conventional wire heaters.

The heel portion of the heater 14 is indicated by numeral 22 and extends into the heel of the boot as shown in FIG. 1. Power for the heater is supplied by batteries 23 that may be incorporated into heel 13 of the boot or, if desired, a battery pack 24 may be detachably carried along the edge of the boot top with electrical conductors extending into connection with the bus lines 15 and 16 of the heater. In many instances, the power source may be carried on the flex circuit heater 14 itself, as suggested by FIG. 2, and an on/off switch 25 may be included.

Figure 3:
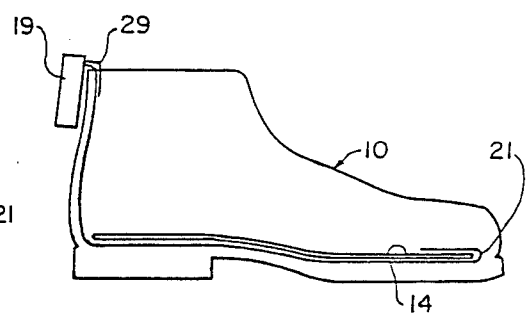
FIG. 3 is a view similar to the view of FIG. 1 illustrating the flex heater of the present invention incorporated into a boot and incorporating a rechargeable power unit.

Referring to FIG. 3, the boot 10 is provided with an external battery pack 26 that is detachably carried about the edge of the boot by means of a clip 27. Therefore, it is to be understood that the flexible heater of the present invention is a separate unit that is integral with respect to its power supply and heating elements so that the heater may be insertably disposed into the interior of the boot so as to lie on the upper surface of the sole 12. Because the heater is composed of a flexible circuit having thin conductive strips, normal movement and stress of the user's foot as it is used during walking or running will not cause weakening of the conductive strip as would be the case if conventional wires were used. The conductive strips are narrow and thin in cross-section so that flexing and bending movements are readily absorbed without stress buildup.

Referring now to FIGS. 4 and 5, the inventive concept of the present invention envisions that the heater 14 may be used in combination with a cushion pad or innersole, such as illustrated in FIG. 4. FIG. 4a illustrates pad 26 having a top surface with a plurality of perforations 27 for the purpose of allowing cross-ventilation for moisture absorption and moisture transfer. However, the underside of the innersole 26 presents a continuous surface 28 which is unperforated. The perforated layer 27 and the unperforated layer 28 are bonded respectively to the opposite sides of an inner neopreme layer identified by numeral 30 in FIG. 5. FIG. 5 also shows that the heater 14 comprises insulative material which surrounds conductive strips and the conductive strip is indicated by numeral 31. The inner layer 30 provides a cushion effect and also serves as a thermal insulator resisting severe temperatures as low as 50° below zero. Also, the pad supports and acts as a correcting agent for slight natural orthopedic imperfections taking up for movement in the X, Y and Z axes. When the multi-ply laminant pad 26 is combined with the boot, the insulative properties from hot and cold are quite noticeable. Also, when combined with the thickness of a boot or shoe, the pad offers a significant insulation against "electrical shock" based on the fact that there is a substantial layer 30 between the user's body and earth ground. The flex cable or circuit heater 14 will mount on the toe of the innersole pad 26 so that the toe portion 20 rests on top and the electrical conductors are bent about the bend line 21. Again, due to the thinness and the width of the individual conductive strips, bending can occur without severing or stressing or fatiguing the conductive strips at the bend line.

Figure 6:
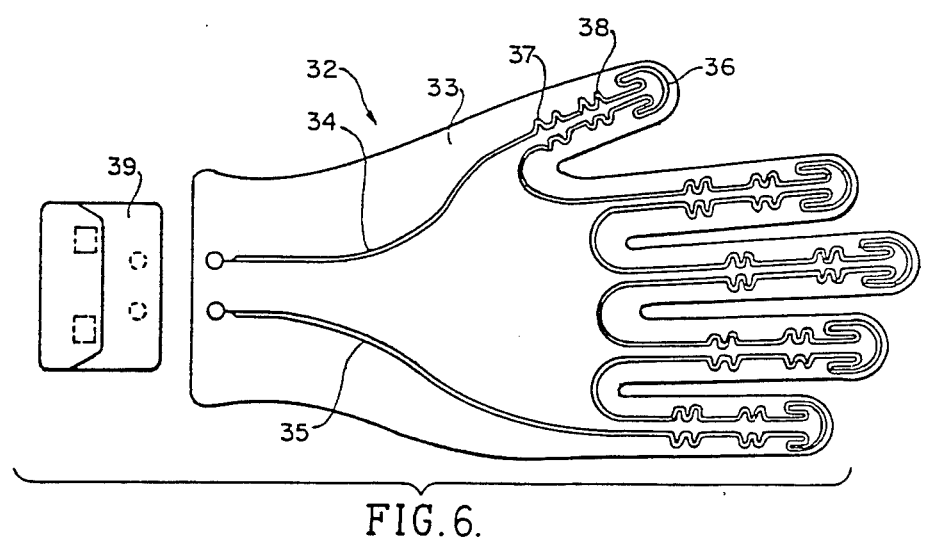
FIG. 6 is a diagrammatic view of another version of flexible heater incorporated into wearing apparel taking the form of a glove insert.

Referring now in detail to FIG. 6, an insert for a glove is illustrated in the general direction of arrow 32 which employs an insulative glove-like sleeve 33 into which the conductive strips are embedded so that the flexible circuitry concept is carried forward. In this embodiment, the bus lines are indicated by numerals 34 and 35 with overlapping loop conductive strips running through the finger portions of the insert and doubling back upon themselves to provide a continuous electrical path. Such a looped configuration of conductive strip is indicated by numeral 36. It is to be particularly noted that each of the conductive strips is formed into an irregular path, such as in a sineusidol path so as to provide a strain relief during flexing of the user's hand while inserted into the glove insert 32. One strain relief is indicated by numeral 37, while another is indicated by numeral 38. These strain relief flex connector configurations are strategically located where the joints of the user's hand would normally reside. Also, a battery pack 39 may be included which can contain a rechargeable battery source or individual storage cells in the case of permanent batteries. The battery pack 39 includes terminals which are intended to match with connector terminals at the ends of the conductor strips 34 and 35 when the glove insert is worn by the user. Again, it is to be understood that the glove insert 32 is intended to be placed inside a conventional glove and is not necessarily recommended for use as a glove per se. Therefore, the insulative material 33 is extremely thin and film-like of sufficient thickness to electrically insulate the low voltage capability of the conductive strips.

Furthermore, the power source package 39 may include a time delay as well as suitable on/off switch means similar to the circuit indicated by numeral 40 in FIG. 2.

In both of the looped electrical strip configurations on the toe portion 20 shown in FIG. 2 and the looped conductive strip portion in each of the fingers of the glove insert 32, are substantially lined in parallel with the lines of force normally experienced by the boot or glove while being worn by the user. Therefore, the circuit lines are in the same direction as the lines of load or physical force encountered by the flex circuit heater.

Referring now in detail to FIG. 7, the circuit 40 is more clearly illustrated, having a power source 41 adapted to be applied to a coil for drawing heater current. The resistance of the coil can be selectively altered by removing a slight portion of the material forming a part of the coil resistance. For example, a plurality of thickened material layers, such as conductive layer 43, may be selectively etched whereby material can be chemically removed so as to alter the resistance of the entire coil to a desired amount. A light 44 indicates that the operation is on and that the heating circuit is complete. The on/off switch 25, when in the off position, represents a charging circuit when a rechargeable transformer 45 is connected to the circuit by means of a jack 46. The switch 25 is a manual switch operable by the user. A load resistor 47 is employed for drawing current.

Another version of the present invention is indicated in FIG. 8 wherein the flexible circuit or cable heater 14 is applied to a toy, such as a teddy bear 50. In this latter instance, the electrical heating circuit is identified by numeral 51 and is placed at the chest of the bear 50 so that when actuated by depression of a button or switch 52, heat from the circuit, such as shown in FIG. 7, will cause the chest of the bear to become warm. Thus, a child holding the bear will feel the warmth of the toy, which is a soothing and desired experience. As in the previous embodiment, the flex circuit heater 51 employs a continuous conductive strip of electrically conductive material which is very thin and wide so as to resist stress and fatigue buildup which would normally break or distort wiring. The conductive strip which is trained in overlapping loops arranged side-by-side is indicated by numeral 53.

In view of the foregoing, it can be seen that the inventive concept includes a novel heater for wearing apparel which is not susceptible to strain or fatigue that would normally sever, break or tear electrical conductors. This stems largely from the fact that the inventive concept includes flexible cable or circuitry involving electrically conductive strips which are broad and flat in plan view and very thin in cross-section so that the conductors may be folded or wrapped about other objects without fatigue or breaking. Also, the arrangement or pattern of the electrical conductive strips is in the line of physical force so that the majority of the loading or stressing is parallel to the run of electrical strips. The flex cable is completed by embedding the plurality of electrical conductive strips in an insulative material such as plastic. The plastic material must be flexible and non-rigid so as to bend or move as applied loads are encountered. As far as a power source is concerned, either permanent storage batteries or rechargeable battery sources may be employed. The light circuit may include a LED and, as mentioned earlier, the resistance of the heater coil 42 can be readily adjusted. For example, heater coil resistance can be within the range of 0.92–1.22 ohms. The resistance of the load resistor 47 may be 470 ohms.

The novel heater incorporated the flex circuit is configured so as to mate with the wearing apparel into which it is inserted. For example, the flex circuit may take the form of the sole of a shoe or boot or may take the form of a glove when it is to be inserted into either one of the these two types of wearing apparel. Also, it is to be understood that when the innersole 26 is employed, a plurality of contour lines representing different shoe or foot sizes can be placed on the upper surface and that the user may cut the innersole to a particular size preparatory for combining with the flexible circuit heater. When properly cut to size, the combined pad and heater can be placed into the properly sized boot or shoe.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A flexible circuit heater adapted for use within an article of clothing or the like, comprising in combination:
    an elongated flat, flexible member of an electrically insulating material, and
    an electrically conductive strip having opposed ends and an interconnecting portion, said strip being wholly embedded within said electrically insulating material of said elongated member,
    said conductive strip traversing at least a major portion of the length of said elongated member with said ends being disposed side-by-side at one end region of said elongated member,
    the interconnecting portion of said conductive strip being disposed in a continuously tortuous pattern of loops at the other end region of said elongated member,
    said other end region of said elongated member being foldable over the adjacent portion of said elongated member major length portion when in use as an article-inserted heater,
    whereby when said elongated member is folded, the continuity of the electrical circuit extending between said one end region and said other end region is maintained during use.

2. The invention as defined in claim 1 including:
    a power source detachably coupled to said contacts; and
    a control switch operably connecting said power source to said conductive strip.

3. The invention as defined in claim 2 including:
    an innersole composed of insulative cushion material lying adjacent to said flexible cable and said toe portion folded over a selected one end of said innersole.

4. The invention as defined in claim 3 wherein:
said flexible cable is configured as a glove for insertion into a conventional glove.

5. The invention as defined in claim 3 including:
an electrical circuit incorporating said power source and said control switch with a heater coil;
said coil having coil thickness adopted to be selectively removed to reduce thickness for adjusting impedence of said coil.

6. The flexible circuit heater of claim 1, wherein said pattern of loops comprises a first plurality of loops and a second plurality of loops,
each of the loops in said first plurality having sides which are disposed substantially parallel to one another, and
the loops of the second plurality being in electrical and physical communication with the loops of the first plurality, said opposed ends of said electrically conductive strip being electrically connected to a selected pair of sides from said first plurality of loops.

7. The flexible circuit heater of claim 6, wherein at least some of the sides of the loops of the second plurality are disposed substantially parallel to the sides of the loops in the first plurality.

8. The flexible circuit heater of claim 7, wherein the remaining loops of said second plurality have sides which are disposed perpendicularly to the sides of the loops of the first plurality.

9. The flexible circuit heater of claim 6, wherein selected ones of the loops in said second plurality have sides which are perpendicular to the sides of the loops in the first plurality.

10. The flexible circuit heater of claim 6, wherein said first plurality of loops is electrically placed between said second plurality of loops and said opposed ends of said electrically conductive strip, but when the flexible cable is folded over for use in an article, said first plurality of loops is physically disposed between said second plurality of loops and said opposed ends of said electrically conductive strip.

11. A heater for use as an insert into wearing apparel comprising:
a length of flat flexible cable having opposite ends and a flat electrically conductive strip extending between the opposite ends of said cable;
said conductive strip having ends, and being continuous between opposite ends of said flat flexible cable, both ends of said continuous strip terminating at one end of said flexible cable in electrical contacts;
said conductive strip extending from said contacts across the length of said flexible cable to a region in which a tortuous path or pattern of loops is defined;
said flexible cable being folded over upon itself in use so that said conductive strip pattern is layered over the conductive strip in an adjacent portion of said flexible cable.

12. In combination with an article of clothing or the like, a flexible circuit heater adapted for use therein, comprising:
an elongated flat, flexible member of an electrically insulating material;
an electrically conductive strip having opposed ends and an interconnecting portion, said strip being wholly embedded within said electrically insulating material of said elongated member;
said conductive strip traversing at least a major portion of the length of said elongated member with said ends being disposed side-by-side at one end region of said elongated member,
the interconnecting portion of said conductive strip being disposed in a continuously tortuous pattern of loops at the other end region of said elongated member,
said other end portion of said elongated member adapted to be folded over the adjacent region of said elongated member major length portion when in use in said article as a heater,
whereby when said elongated member is folded over, said conductive strip is protected against breakage by said insulating material such that the continuity of the electrical circuit extending between said one end region and said other end region is maintained during use.

13. The combination of claim 12, wherein said article comprises a shoe or the like having an insole, and said flexible heater is disposed in the interior of the article adjacent to and lying on said insole.

14. The combination of claim 12, wherein said article comprises a glove or the like, and said flexible heater is fashioned as a glove insert which, when used with said article, is inserted therewithin.

15. The combination of claim 14, wherein said glove and said glove insert both have individualized finger-covering regions, and said pattern of loops being located in said finger-covering regions of said glove insert.

* * * * *